US009801854B1

(12) United States Patent
Strauss-Ayali et al.

(10) Patent No.: US 9,801,854 B1
(45) Date of Patent: Oct. 31, 2017

(54) SLOW RELEASE FORMULATIONS OF CELL CYCLE REGULATORS AND ANTI-CANCER AGENTS FOR LOCAL TREATMENT OF SOLID CANCER

(71) Applicant: THERACOAT LTD., Ra'anana (IL)

(72) Inventors: Dalit Strauss-Ayali, Sde Warburg (IL); Gil Hakim, Ra'anana (IL); Marina Konorty, Herzliya (IL); Astar Friedman, Petah Tikva (IL)

(73) Assignee: UROGEN PHARMA LTD., Raanana (IL)

( * ) Notice: Subject to any disclaimer, the term of this patent is extended or adjusted under 35 U.S.C. 154(b) by 0 days.

(21) Appl. No.: 14/600,354

(22) Filed: Jan. 20, 2015

Related U.S. Application Data

(60) Provisional application No. 61/928,594, filed on Jan. 17, 2014.

(51) Int. Cl.
*A61K 47/34* (2017.01)
*A61K 31/407* (2006.01)
*A61K 31/17* (2006.01)
*A61K 47/38* (2006.01)
*A61K 47/32* (2006.01)

(52) U.S. Cl.
CPC ............ *A61K 31/407* (2013.01); *A61K 31/17* (2013.01); *A61K 47/32* (2013.01); *A61K 47/34* (2013.01); *A61K 47/38* (2013.01)

(58) Field of Classification Search
CPC ..................................... A61K 47/34
See application file for complete search history.

(56) References Cited

U.S. PATENT DOCUMENTS

| 2004/0009212 A1 * | 1/2004 | Tsai | ............... A61K 9/006 424/449 |
| 2009/0142259 A1 * | 6/2009 | Gao | ............... G01N 33/57407 514/1.1 |

FOREIGN PATENT DOCUMENTS

EP  0386960 A2 * 9/1990 ........... A61K 9/0014

OTHER PUBLICATIONS

Ta et al (Journal of Controlled Release 126 (2008) 205-216).*

* cited by examiner

*Primary Examiner* — Benjamin Packard
(74) *Attorney, Agent, or Firm* — JMB Davis Ben-David

(57) ABSTRACT

Provided herein are methods for treating cancer of a body cavity, including specifically urinary tract cancer, by way of at least one cell cycle regulator, and at least one anti-cancer drug for local treatment; wherein the therapeutic agents are embedded in, and slowly released from, a biocompatible hydrogel composition.

14 Claims, 16 Drawing Sheets

| G0/G1 | S | G2/M |
|---|---|---|
| 62.3 | 16.5 | 15.9 |

| G0/G1 | S | G2/M |
|---|---|---|
| 59 | 19.2 | 19.7 |

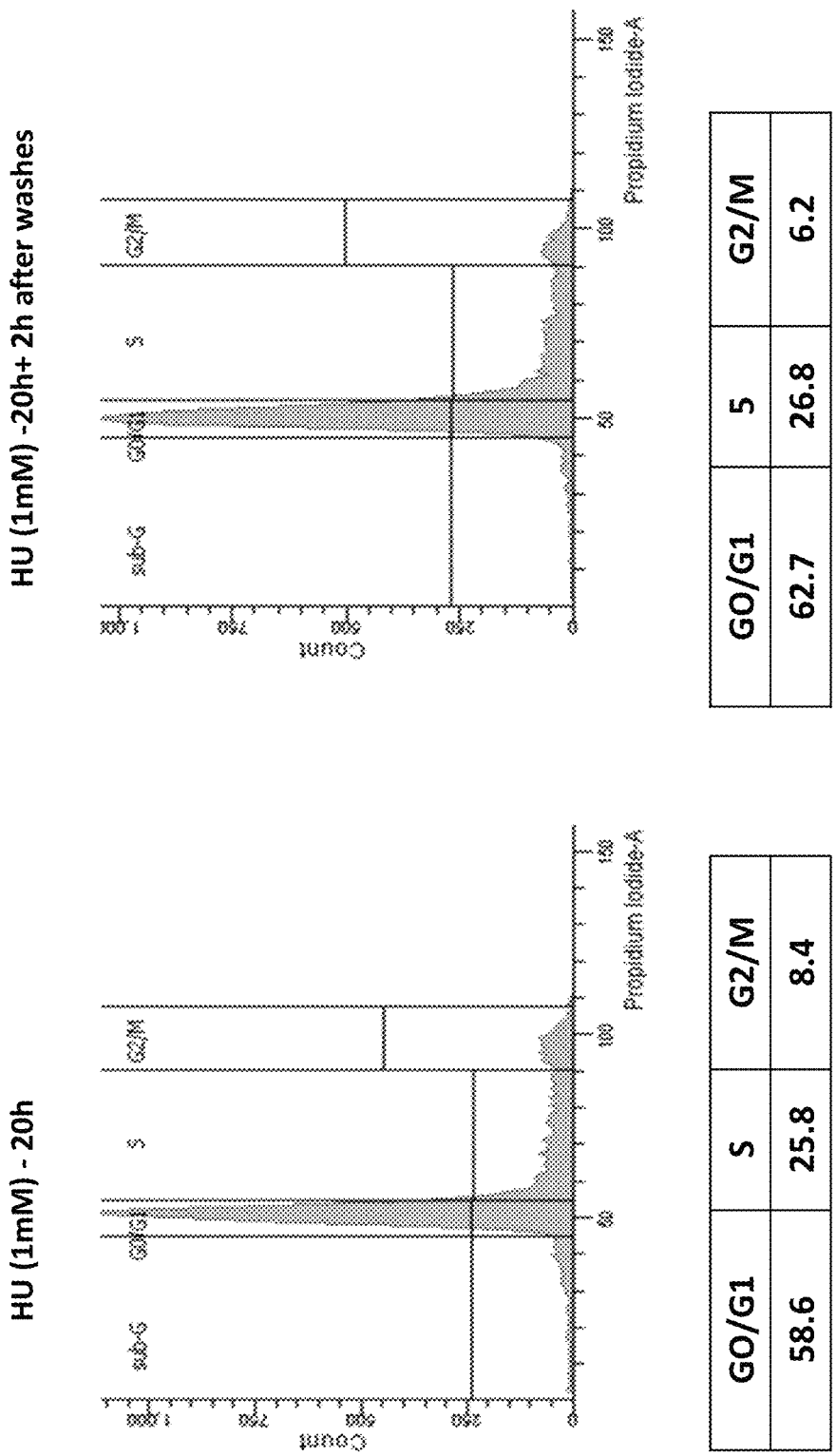
Figure 1A – Continuation I

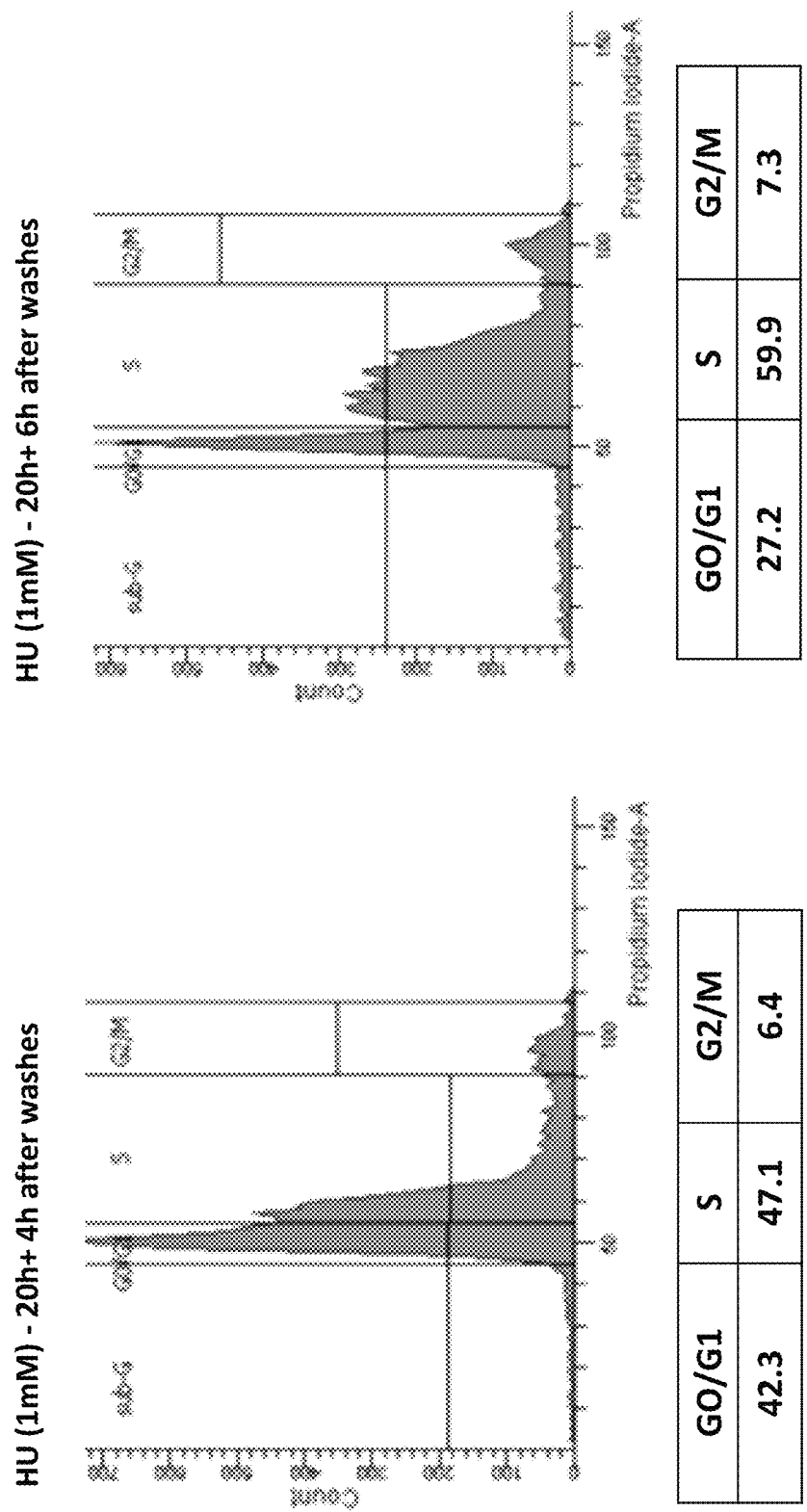
Figure 1A – Continuation II

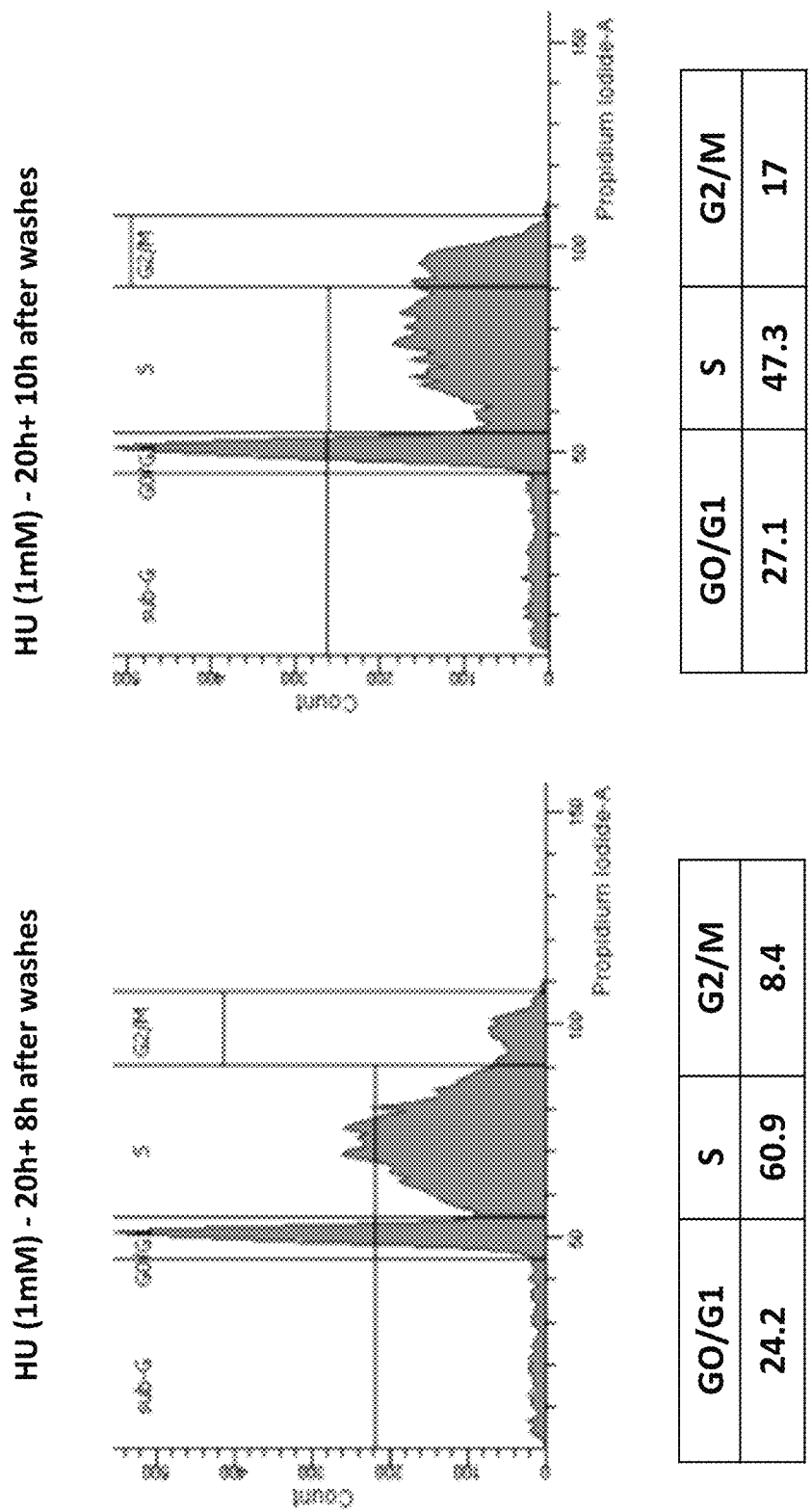
Figure 1A – Continuation III

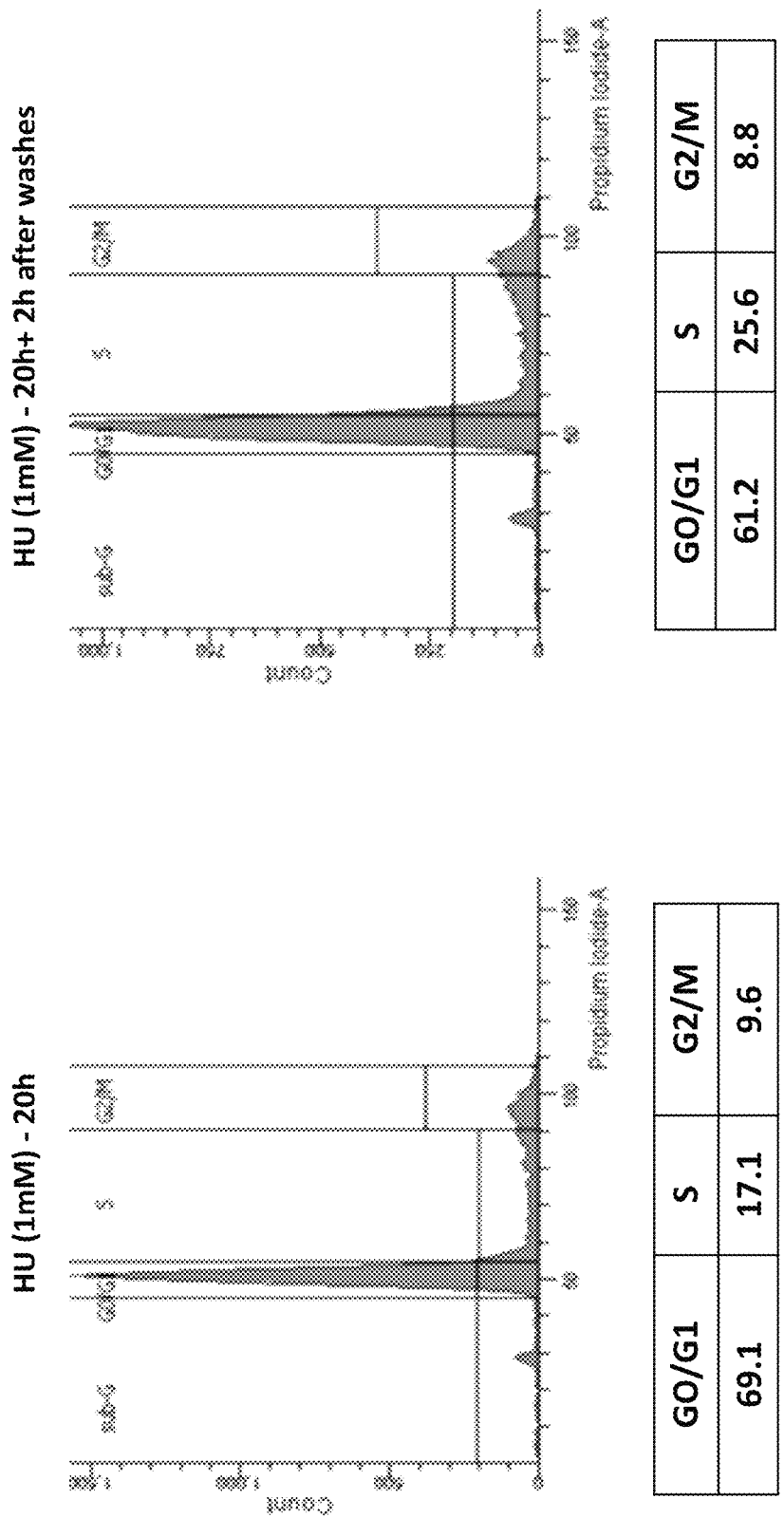
Figure 2A – Continuation I

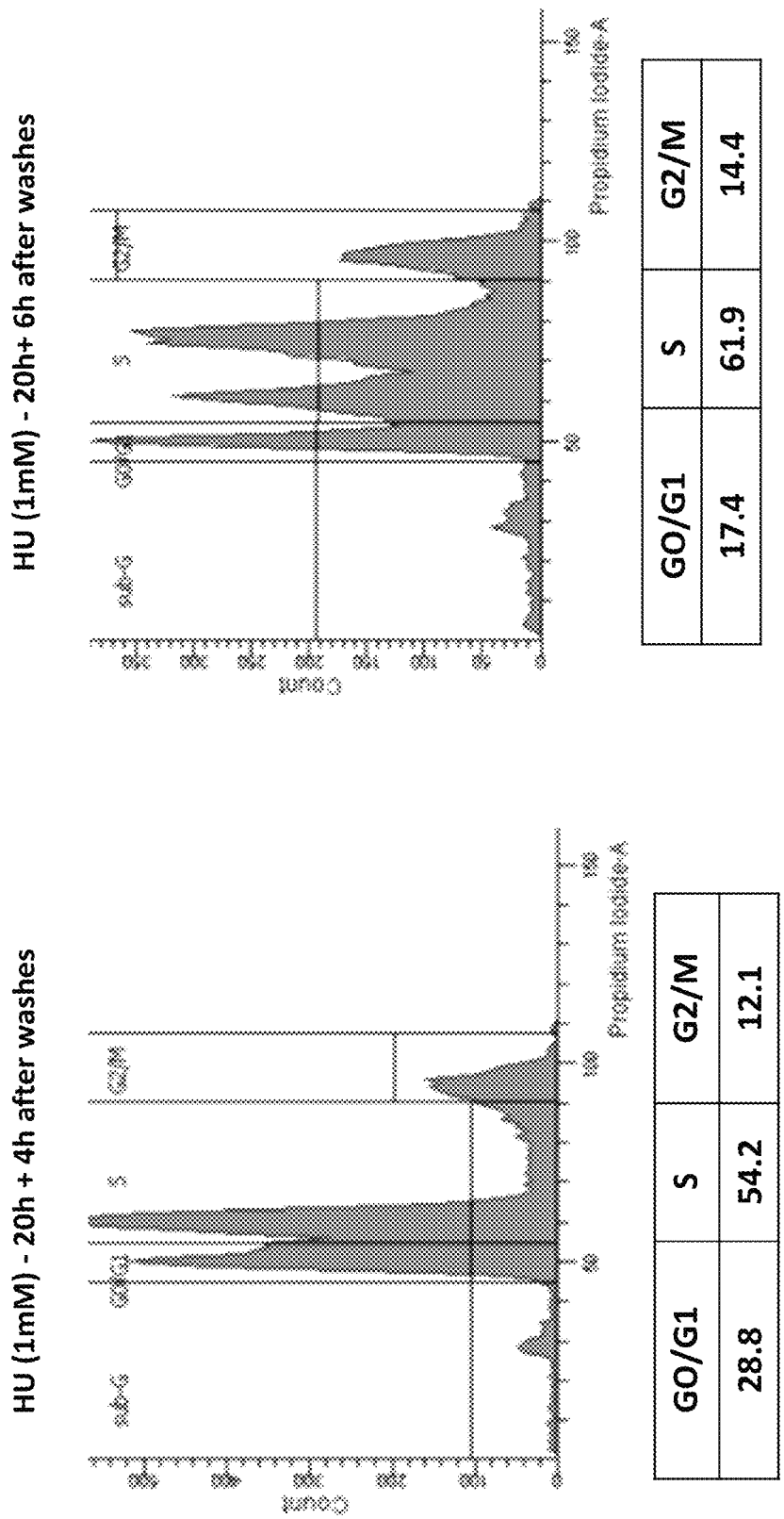
Figure 2A – Continuation II

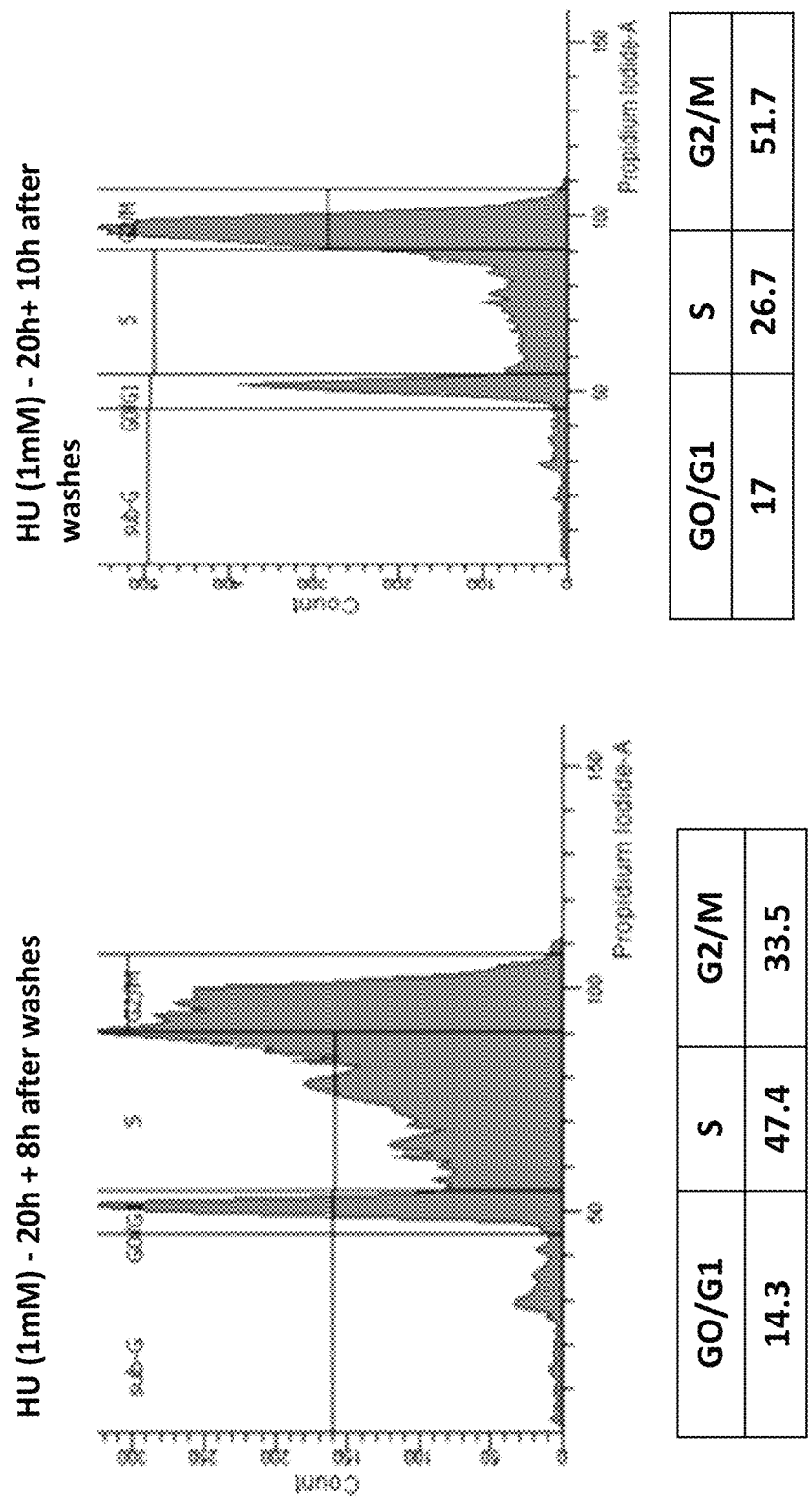
Figure 2A – Continuation III

SLOW RELEASE FORMULATIONS OF CELL CYCLE REGULATORS AND ANTI-CANCER AGENTS FOR LOCAL TREATMENT OF SOLID CANCER

CROSS REFERENCE TO RELATED APPLICATIONS

Benefit is claimed to U.S. Provisional Patent Application No. 61/928,594, filed Jan. 17, 2014, which is incorporated by reference herein in its entirety.

FIELD

Provided herein are methods for treating cancer, specifically urinary tract cancer, by way of at least one cell cycle regulator, and at least one anti-cancer drug for local treatment; wherein the therapeutic agents are embedded in, and slowly released from, a biocompatible hydrogel composition.

BACKGROUND

Cancers are diseases of uncontrolled proliferation of abnormal cells. Urothelial carcinoma of the urinary bladder represents more than 90% of all bladder cancers, about 80% of which are non-muscle invasive bladder cancer (NMIBC), a form of superficial cancer. Transurethral resection and radical cystectomy remain the mainstay of treatment for NMIBC and MIBC (muscle invasive bladder cancer), respectively. Intravesical therapy of Bacillus calmette-Guerin (BCG) and mitomycin are preferable adjuvant therapies to surgery aiming at reducing disease recurrence and progression. The major drawback for intravesical instillation is the short exposure time of tissue to the drug due to urine creation and voiding that dilutes and displaces drug from the area of treatment.

It is well known that malignant neoplasms consist of heterogeneous cells which proliferate asynchronously. As a result, administered cytotoxic drugs will affect only those malignant cells that are at the specific cell cycle phase at which the drug is most efficacious. The rest of the cells will be affected only if the exposure time is long enough to permit the cells to cycle to the phase sensitive to the specific chemotherapeutic drug. In the bladder and other body cavities of continual secretion and voiding, exposure time of a cancer target to cytotoxic drugs will be limited. Therefore, the treatment efficiency will be relatively low and will require repeating treatment sessions.

Thus there remains a need for improvements in delivery and efficacy of non-surgical cancer treatments of cancers in secreting and voiding areas of the body such as the urinary tract, and particularly the bladder.

The present invention therefore seeks to provide new combinations of cell cycle regulators and at least one anti-cancer agent for the treatment of proliferative disorders, especially cancer. More specifically, the invention relates to unexpected effects associated with increased efficacy for treating cancer while using cell cycle modifiers and at least one anti-cancer agent, each embedded in a thermoreversible hydrogel matrix and locally administered to the affected body cavity, such as by intravesical means.

SUMMARY

It has been discovered that sustained local treatment of a body cavity cancer using a cell cycle modulator (CCM), followed by sustained local treatment with a chemotherapeutic agent can provide a superior cytotoxic, anti-cancer effect comparison to treatment with either agent alone.

Among the many cellular components involved in cell cycle regulation are the cyclin dependent kinases (CDKs) inhibitors. CDKs inhibitors are known to arrest cell at different phases of the cell cycle i.e. G1 or G2/M and in some cases induce apoptosis. Various S phase arresting agents can also play a significant role in cell cycle regulation.

The fluid-filled environment of many body cavities presents a challenge to achieving such sustained treatments. Therefore, the methods of treatment provided herein utilize hydrogel compositions having reverse thermal gelation (RTG) properties which enable a liquid mixture with a specific drug, and application to a body internal cavity at a temperature below its gelation point, and which solidifies at body temperature (such compositions herein are also referred to as a "thermoreversible hydrogel"). The hydrogel composition is mixed with the specific active pharmaceutical agents to produce compositions for local sustained treatment.

Accordingly, described herein are methods for treating a cancer of a body cavity which involves the sequential local administration of active agents to the body cavity surface. In a first step, a first composition comprising a thermoreversible hydrogel composition and a therapeutically effective amount of at least one cell cycle modulator is administered locally, such as intravesically to the subject. In the second step, a second composition comprising a thermoreversible hydrogel composition and a therapeutically effective amount of at least one chemotherapeutic agent is administered locally to the surface of the body cavity. The sustained sequential treatment of the surface of the body cavity with the CCM and the chemotherapeutic agents provides treatment of a cancer on the surface of the body cavity.

Various embodiments of the provided methods that provide for administrations of a variety of agents, in a variety of thermoreversible hydrogels, and in a variety of administration timing regimes, are also provided herein.

The foregoing and other objects, features, and advantages will become more apparent from the following detailed description, which proceeds with reference to the accompanying figures.

BRIEF DESCRIPTION OF THE DRAWINGS

FIG. 1A Shows cell cycle analysis as done by flow cytometry. UM-UC3 cells were cultured with 1 mM hydroxyurea for 20 hours or with DMSO (vehicle control) for 24 hours. After 20 hours (24 hours for DMSO treated cells), the hydroxyurea (or DMSO) was washed and replaced by fresh media and cells were fixed and labeled with propidium iodide (PI) between 2 to 10 hours following washes. The data indicate the percentage of cells in each phase of the cell cycle. FIG. 1B shows a graphical representation of the percentage of cells in S phase at the indicated times following washing.

FIG. 2A Shows cell cycle analysis as done by flow cytometry. RT-4 cells were cultured with 1 mM hydroxyurea for 20 hours or with DMSO (vehicle control) for 24 hours. After 20 hours (24 hours for DMSO treated cells), the hydroxyurea (or DMSO) was washed and replaced by fresh media and cells were fixed and labeled with PI between 2 to 10 hours following washes. The data indicate the percentage of cells in each phase of the cell cycle. FIG. 2B shows a graphical representation of the percentage of cells in S phase at the indicated times following washing.

DETAILED DESCRIPTION

Figure 1A:
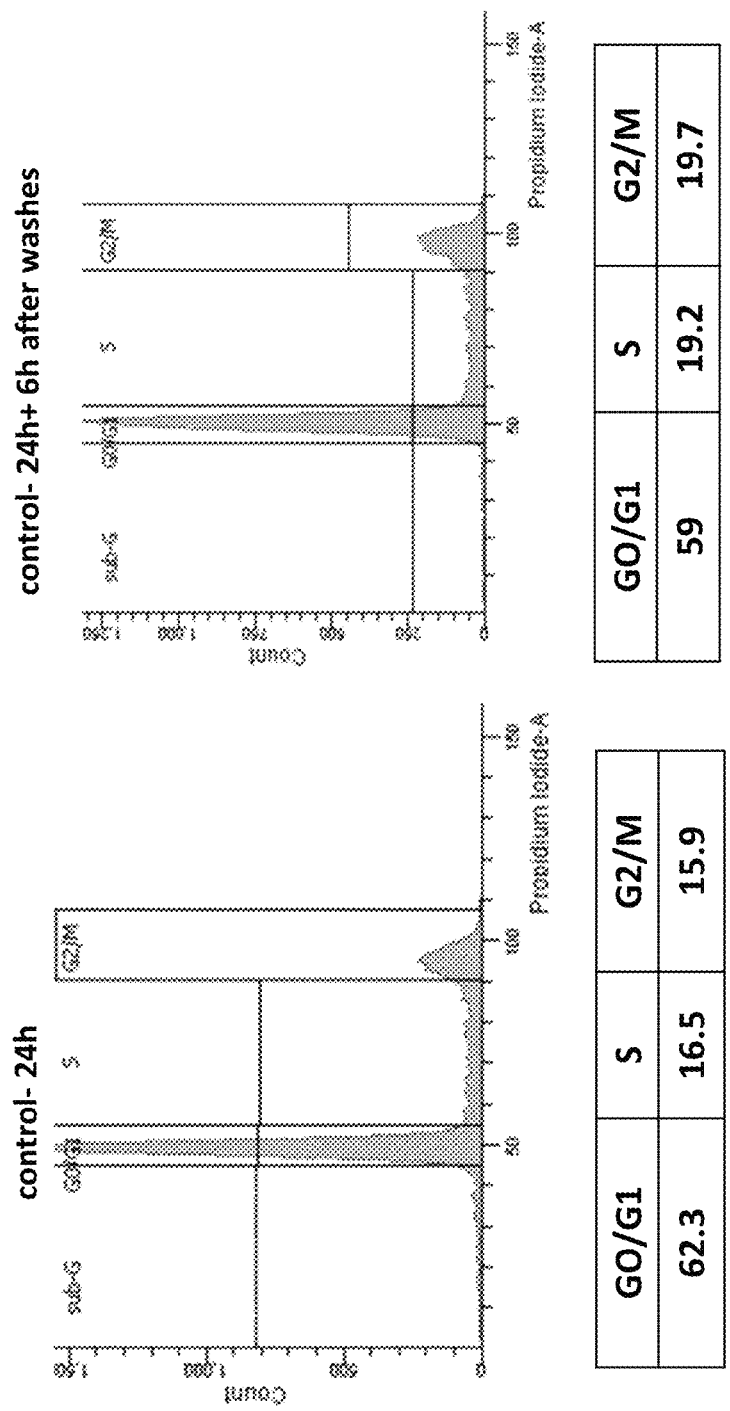
FIGS. 1A and 1B show cell cycle arrest in S phase following exposure of UM-UC3 cells to hydroxyurea.

Unless otherwise noted, technical terms are used according to conventional usage. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8

I. Abbreviations

CCM Cell cycle modulator
HU Hydroxyurea
HPMC Hydroxyl propylmethyl cellulose
MMC Mitomycin C
PEG Polyethylene glycol
PEO Polyethylene oxide
PVP Polyvinylpyrrolidone
PPO Polypropylene oxide

II. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that as applicable, all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example." In case of conflict, the present specification, including explanations of terms, will control. In addition, all the materials, methods, and examples are illustrative and not intended to be limiting.

Administration: The introduction of a composition into a subject by a chosen route. Administration of an active compound or composition can be by any route known to one of skill in the art, and as appropriate for the compound and the delivery system. For example, the compositions for use in the described methods are typically administered locally to the inside surface of a body cavity, such as by intravesical instillation.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound. It is acknowledged that these terms may overlap in some circumstances. In particular embodiments of the claimed methods, analogs, derivatives, or mimetics having comparable activity to the expressly recited compounds can be used in place of the recited compounds.

Animal: Living multi-cellular vertebrate organisms, a category that includes for example, mammals and birds. The term mammal includes both human and non-human mammals. Similarly, the term subject includes both human and veterinary subjects, for example, humans, non-human primates, dogs, cats, horses, and cows. The term "primate" includes both human and non-human primates. "Non-human primates" are simian primates such as monkeys, chimpanzees, orangutans, baboons, and macaques. Similarly, the term "subject" includes both human and veterinary subjects, such as non-human primates, which have internal body cavities for which the described methods can be of benefit.

Body cavity: Any fluid-filled space internal to a multicellular organism. In particular embodiments, a body cavity can include other body cavities. For example, the mammalian pelvic cavity includes the bladder, and the thoracic cavity includes the upper gastro-intestinal tract and cavities such as the esophagus. In particular embodiments, a body cavity can be the urinary tract, such as the bladder.

Cancer: A malignant disease characterized by the abnormal growth and differentiation of cells. The product of neoplasia is a neoplasm (a tumor or cancer), which is an abnormal growth of tissue that results from excessive cell division. A tumor that does not metastasize is referred to as "benign." A tumor that invades the surrounding tissue and/or can metastasize is referred to as "malignant." Neoplasia is one example of a proliferative disorder. A "cancer cell" is a cell that is neoplastic, for example a cell or cell line isolated from a tumor.

Examples of solid tumors, such as sarcomas and carcinomas, and which include cancers of internal body cavities, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers (such as small cell lung carcinoma and non-small cell lung carcinoma), ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma, astrocytoma, medulloblastoma, craniopharyogioma, ependymoma, pinealoma, hemangioblastoma, acoustic neuroma, oligodendroglioma, menangioma, neuroblastoma and retinoblastoma).

Cell cycle: The cycle of cellular division, which consists of M phase, G1 phase, S phase, and G2 phase. During S phase (synthesis), the cell replicates its DNA, doubling the cell DNA content. The period from the end of DNA replication until mitosis is G2 (gap 2) during which the cell nucleus contains two sets of chromosomes (also referred to as 4N state). M phase is mitosis, during which the duplicated chromosomes are separated and two daughter cells are formed. Once M phase is complete, the cell enters G1 phase (gap 1), during which RNAs and proteins are synthesized and cell size increases.

Progression through the cell cycle is tightly regulated by cell cycle checkpoints, control mechanisms that ensure that each phase of the cell cycle has been accurately completed prior to progression to the next phase. In particular, there are three major cell cycle checkpoints: G1/S checkpoint (also known as the "restriction point" in animal cells or the "start point" in yeast cells), G2/M checkpoint, and anaphase checkpoint.

Cells undergo "cell cycle arrest" when they are blocked from progression through the cell cycle. In a particular example, cells are arrested in the cell cycle prior to mitosis. "Cell cycle modulators" are agents that synchronize and/or arrest cells at a particular cell cycle phase, such as at the G1 and S-phase or at any of the cell cycle checkpoints known in the art.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a bladder cancer, a urinary cancer, or another tumor, such as an anti-neoplastic agent. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., Chemotherapy, Ch. 17 in Abeloff, *Clinical Oncology* 2nd ed., 2000 Churchill Livingstone, Inc; Baltzer and Berkery. (eds): *Oncology Pocket Guide to Chemotherapy*, 2nd ed. St. Louis, Mosby-Year Book, 1995; Fischer Knobf, and Durivage (*eds*): *The Cancer Chemotherapy Handbook,* 4th ed. St. Louis, Mosby-Year Book, 1993). Common chemotherapeutic agents include mitomycin C, valrubicin, thiotepa, ethoglucid (epodyl), pirarubicin, apaziquone, vicinium, interleukin-2, cisplatin, paclitaxel, docetaxel, doxorubicin, epirubicin, topotecan, irinotecan, mitomycin, iazofurine, gemcitabine, etoposide, vinorelbine, tamoxifen, valspodar, cyclophosphamide, methotrexate, fluorouracil, mitoxantrone, and vinorelbine. Combination chemotherapy is the administration of more than one agent to treat cancer.

Contacting: Placement in direct physical association. Includes both in solid and liquid form. Contacting can occur in vitro with isolated cells or in vivo by administering to a subject.

Control: A reference standard. In particular examples a control sample is taken from a subject that is known not to have a disease or condition. In other examples a control is taken from the subject being diagnosed, but at an earlier time point, either before disease onset or prior to or at an earlier time point in disease treatment.

Effective amount of a compound: A quantity of compound sufficient to achieve a desired effect in a subject being treated. An effective amount or "therapeutically effective amount" of a compound can be administered in a single dose, or in several doses, for example daily, during a course of treatment. However, the effective amount of the compound will be dependent on the compound applied, the subject being treated, the severity and type of the affliction, and the manner of administration of the compound.

Intravesical instillation: Also known as "intravesical therapy;" a medical procedure involving the direct administration of a drug into the bladder. Comparable drug administration is possible for other body cavities. In particular embodiments, intravesical instillation involves delivery of a drug through a catheter. In particular embodiments of the methods described herein, hydrogel-based compositions are provided to a subject by intravesical instillation.

Pharmaceutically acceptable carriers: The active agents for use in the described methods can be, mixed with a pharmaceutically acceptable carrier. The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Preventing or treating a disease: Preventing a disease refers to inhibiting the full development of a disease, for example inhibiting the development of myocardial infarction in a person who has coronary artery disease or inhibiting the progression or metastasis of a tumor in a subject with a neoplasm. Treatment refers to a therapeutic intervention that ameliorates a sign or symptom of a disease or pathological condition after it has begun to develop. Preventing and treating a disease can also refer to the results of interventions taken to prevent the recurrence of a disease that has been otherwise treated, such as surgery to remove a solid tumor in an internal body cavity.

Subject susceptible to a disease or condition: A subject capable of, prone to, or predisposed to developing (or redeveloping) a disease or condition. It is understood that a subject already having or showing symptoms of a disease or condition is considered "susceptible" since they have already developed it.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, or antibody) in blood (in vivo) or a buffer (in vitro) that produces an effect.

Thermoreversible hydrogel: Non-fluid hydrophilic polymer network. The thermoreversible hydrogels for use in the described methods are in liquid form at room temperatures and remain liquid in the process of administration to a patient (e.g. through intravesical instillation). At elevated temperatures (e.g. typical human body temperature), thermoreversible hydrogel solidifies, such as in a coating of an internal body cavity.

Urinary tract cancer: Cancer of any area of the urinary tract, including the kidney, ureter, bladder (also referred to as "urinary bladder"), and urethra. Common forms of bladder cancer include transitional cell carcinoma, inverted papilloma, and Squamous-cell carcinoma. Surgery followed by intravesical instillation of chemotherapy is a common treatment for urinary tract solid tumors.

Wash: Use of a fluid to cleanse an area. In particular embodiments, the "wash" of an area results in complete cleansing of the area. In other embodiments, washing an area does not produce complete cleansing. In particular embodiments of the described methods, a body cavity is "washed" between application of compositions containing a hydrogel and a therapeutic agent. In particular embodiments, the composition is completely washed out of the body cavity. In other embodiments, the composition is not completely washed out of the body cavity. The wash (and removal of fluid) of the methods described herein can be accomplished by standard methods of introducing and removing fluid from a body cavity.

III. Overview of Several Embodiments

Described herein is a method for treating a cancer of a body cavity by administering to a subject in need of such treatment, a first composition that includes a thermoreversible hydrogel composition and a therapeutically effective amount of at least one cell cycle modulator; followed by administering to the subject a second composition that includes a thermoreversible hydrogel composition and a therapeutically effective amount of at least one chemotherapeutic agent, wherein the administration of the first and second compositions is by local administration to the body cavity, and the administration of the compositions treats the cancer.

In particular embodiments of the described method, the cancer of the body cavity is a urinary tract cancer, such as bladder cancer.

In other particular embodiments, the thermoreversible hydrogel composition in the first and second compositions is the same, while in other embodiments, the thermoreversible hydrogel compositions of the first and second compositions are different.

In particular embodiments, the second composition optionally comprises the hydrogel composition and can include the chemotherapeutic agent in a non-hydrogel solution.

In certain embodiments, the thermoreversible hydrogel composition of the first and/or second compositions includes: 20% to 40% (w/w) EPO/PPO block copolymer; 0.05% to 0.5% (w/w) hydroxypropylmethylcellulose (HPMC) or Polyvinylpyrrolidone (PVP); 0.1% to 2.5% (w/w) polyethylene glycol (PEG)-400; and the balance water.

In particular embodiments of the described method, the cell cycle modulator synchronizes the cells that it contacts in the G1 and the S phases. For example, the cell cycle modulator can be selected from the group consisting of: hydroxyurea, alternol, resveratrol, fluorodeoxyuridine, thymidine dinucleotide pTpT and Zidovudine, PD-0332991, LEE011, CINK4, Flavopiridol p276-00 and P1446A-05.

In some embodiments, the chemotherapeutic agent is selected from the group consisting of: Mitomycin C, Apaziquone, Gemcitabine, Cisplatin, 5-FU (5-fluorouracil) Doxorubicin, Valrubicin, Epirubicin, Pirarubicin, Methotrexate and analogs thereof.

Administration of the compositions in the described method is by local administration. In particular embodiments, the local administration is by intravesical instillation.

In some embodiments of the described method, the second composition is administered to the subject 2-72 hours after administration of the first composition.

In particular embodiments of the described method, the first composition is allowed to remain in the body cavity for at least 2 hours, and is then washed from the body cavity prior to administration of the second composition. In some embodiments, the second composition is administered immediately after the first composition is washed from the body cavity. In other embodiments, the second composition is washed after a defined period of time, up to 72 hours after the first composition is washed from the body cavity.

In still other embodiments of the described method, the first and second compositions are provided to the body cavity following a surgery performed to remove the cancer being treated by the compositions.

IV. Methods for Sequential Sustained Treatment

Described herein are methods for treating a cancer found in or on the surface of an internal body cavity, such as a cavity of the urinary tract. The methods involve sequential administration of at least two compositions, the basis of both of which is a hydrogel with reverse thermal gelation properties, such that the gel is in solid gel form at an internal body temperature and in liquid form at reduced temperatures, such in a any temperature below 18° C.

The first composition which is administered onto the surface of the internal body cavity is composed of a thermoreversible hydrogel combined with a cell cycle modulator (CCM), which synchronizes or arrests contacted cells at a particular phase of the cell cycle, such as but not limited to the G1 and S phases. Particular examples of cell cycle modulators include: CDKs (cyclin-dependent kinases) inhibitors and S phase arresting agents. Inhibitors of CDKs such as CDK1, 2, 4, or CDK 6 include but are not limited to PD-0332991, LEE011, CINK4, flavopiridol, p276-00 and P1446A-05. S phase arresting agents include small molecules such as but not limited to Hydroxyurea, Alternol, Resveratrol, Fluorodeoxyuridine, Thymidine dinucleotide pTpT, Zidovudine.

After a sufficient period of time for the CCM to take effect, a second composition is applied to the surface of the body cavity. The second composition is composed of a thermoreversible hydrogel combined with an anti-cancer agent, such as a chemotherapeutic cytotoxic agent, an antineoplastic agent (referred to collectively as "chemotherapeutic agents")

The localized, sequential, and sustained administration of the CCM and chemotherapeutic agents provides an enhanced cytotoxic effect which more effectively treats the target cancer than any of the agents applied alone, whether or not administered in a thermoreversible hydrogel composition.

In a particular embodiment, the body cavity is any internal body cavity that produces and/or voids fluid in such a way that locally administered agents are quickly flushed from the site of administration. Particular examples of such cavities include the bladder, the upper urinary tract (including: the ureters, renal pelvis and calyces) abdomen, and the gastrointestinal tract.

In particular embodiments the cancer is a solid cancer found on or in the surface of an internal body cavity. Particular non limiting examples include bladder cancer, urinary tract, gastrointestinal cancer, vaginal cancer, rectal cancer, thoracic cancer, and pelvic cancer.

The methods described herein administer the described compositions in a particular sequence, such that the composition containing the CCM ("first composition") is administered prior to the composition containing the chemotherapeutic agent ("second composition"). In the preferred embodiment the first composition administered 2-36 hours prior to the second composition. In more preferred embodiment the first composition administered 12-24 hours prior to the second composition.

Because the first and second compositions provide the active agents in a thermoreversible hydrogel, the compositions can remain associated with the local area of administration for an extended period of time. In particular embodiments, the first and second compositions are allowed to remain in contact with the body cavity under treatment for the same amount of time. In other embodiments, the compositions remain in contact with the body cavity for different times. In particular embodiments, the first composition remains in contact with the body cavity for a longer period of time than the second composition. In other embodiments, the second composition remains in contact with the body cavity for a longer period of time. In still other embodiments, the first composition is in contact with the body cavity for a specified period of time, whereas the second composition contacts the body cavity for an undefined period. The duration of treatment (and therefore of contact of each composition with the body cavity) in any of these embodiments can be hours or even days at a time.

In particular embodiments, the compositions can contact the body cavity for up to 48 hours, up to 36 hours, up to 24 hours, up to 22 hours, up to 20 hours, up to 18 hours, up to 16 hours, up to 14 hours, up to 12 hours, up to 10 hours, up to 8 hours, up to 4 hours, and up to 2 hours. In other embodiments, the compositions can contact the body cavity for up to 3, 4, 5, 6, 7 or more days.

In still other embodiments, the compositions can contact the body for at least a certain amount of time, such as at least 2-48 hours, such as at least 2, at least 4, at least 6, at least 8, at least 10, at least 12, at least 14, at least 16, at least 18, at least 20, at least 22, at least 24, at least 36, at least 48 hours, or more.

In particular embodiments wherein one or more of the compositions contacts the body for a minimal amount of time (e.g. less than 4 hours, such as less than 3, 2, or 1 hour), the active ingredient (one or both of the CCM or the chemotherapeutic agent) need not be provided in a hydrogel composition, but may be administered locally, such as by instillation, as is known in the art. In such embodiments for example, the chemotherapeutic agent can be provided in solution by local administration (in solution, such as by instillation) after the cells have been synchronized by in-gel administration of the CCM.

The administration of the first and second compositions is sequential; one following the other. In particular embodiments, the second composition is applied to the body cavity after a sufficient time has elapsed such that the first composition has fully degraded and is no longer associated with the body cavity. In other embodiments, the first composition is washed out of the body cavity either by urination or by active washing prior to administration of the second composition. Such active washes can be achieved with any biocompatible solution known to the art.

In particular embodiments, following the wash or degradation of the composition, the second composition can be immediately administered to the body cavity. In other embodiments, the second composition is only administered after a specified period of time has elapsed. In particular embodiments, the second composition is administered from 1-48 hours after the wash or degradation (and removal of the first composition from the body cavity). For example, the second composition can be administered 2-36 hours after the wash, such as 2, 4, 6, 8, 10, 12, 14, 16, 18, 20, 22, 24 hours after the wash.

In particular embodiments, more than two compositions are applied sequentially to the subject. One of skill will appreciate that the time which each composition in such methods can be applied to the body cavity can be any of the times described herein. Likewise, a sequence of washing steps of equal or varying duration can be included in such methods between administrations of each composition.

In particular embodiments, after the specified period of time, the second (or last in the case of more than two compositions) composition is washed from the internal body cavity. The washing solution can be the same or different from a solution used to wash the first composition from the body cavity.

The described methods locally administer active pharmaceutical agents in compositions that include a gel having reverse thermal gelation properties (a "thermoreversible hydrogel"). In particular embodiments, the thermoreversible hydrogel composition includes one or more components including poloxamer, methylcellulose, hydroxypropylmethylcellulose, alginates, cellulose acetophathalate, carbopol, gellan gum, xyloglucan, pectin, chitosan, and any combination thereof.

In particular embodiments the gel component of the thermoreversible hydrogel compositions comprises 5%-45% (w/w) and ranges therein of the composition, such as 10%-35%, 20%-45%, 15%-35%, 20%-40%, 20%-30%.

In particular embodiments the thermoreversible hydrogel comprises an A-B-A type polymer, wherein A or B is selected from PEG (polyethylene glycol), PLGA (poly(lactic-co-glycolic) acid, PLA (polylactic acid) and PPO (polypropylene oxide). More preferably, A is PEG and B is PPO (poloxamer) compound or A-B-A is PEO (Poly(ethylene oxide)/PPO block copolymer.

In a particular embodiment the thermoreversible hydrogel composition comprises 5% to 45% (w/w), and any range therein, of a PEO/PPO block copolymer and comprises at least one of a mucoadhesive enhancing agent, dissolution rate controlling agent, gelation temperature controlling agent, pH controlling agent, absorption enhancer/tight junction modifier/cell membrane permeability enhancer, pharmacodynamics enhancing agent, or an agent to produce an exothermic reaction.

In particular embodiments, the mucoadhesive enhancing agent can include, but is not limited to, agarose, chitosan, gelatin, hyaluronic acid, carrageenan, pectin, sodium alginate, polyacrylic acids, polymers based on poly(meth)acrylic acid, carbopol, polycarbophil, polyacrylic acid, polyacrylates, copolymer of acrylic acid and polyethylene glycol, copolymer of methylvinyl ether and methacrylic acid, poly-2-hydroxyethylmethacrylate, copolymer of acrylic acid and ethylhexylacrylate, polymethacrylate, poly-alkylcyanoacrylates: polyisobutylcyanoacrylate, polyisohexylcyanoacrylate, cellulose derivatives (for example methylcellulose (MC), hydroxy-propylcellulose (HPC), hydroxyl propylmethyl cellulose (HPMC), hydroxy ethyl cellulose, thiolated CMC other hydroxyalkylcelluloses and hydroxyalkylmethylcelluloses, carboxy-methylcelluloses (CMC) and salts thereof), polymethacrylates, starch or starch derivatives including starch phosphate esters at various degrees of substitution, as well as gums like guar gum, locust beam gum and xanthan gum and their derivatives. Polyvinylpyrrolidone (PVP) and its copolymers (N-vinyl-2-pyrrolidone), Poly-N-2-hydroxypropylmethacrylamide, polyhydroxyethylene, polyvinyl alchohol (PVA), and thiolated polymers.

In particular embodiments, dissolution rate controlling agents can include, but are not limited to, silicon dioxide or any derivatives thereof, nanoparticles or microparticles of Poly (Lactide-co-Glycolide) (PLGA), polylactic acid (PLA), Polyglycolic acid (PGA), PLA-PEG or PLGA-PEG copolymers, nanoparticles or microparticles polystyrene or polymethyl methacrylate (PMMA), calcium carbonate, microcrystalline cellulose, aluminum hydroxide, Eudragit® NE, Eudragit® RS and RL, cellulose acetate and cellulose acetate butyrate, crospovidones, crosslinked sodium carboxymethylcellulose, crosslinked sodium carboxymethyl-starch, thickening agents, soy, iodinated aromatic compounds, cyclodextrin, and cholesterol.

In particular embodiments, gelation temperature controlling agents include, but are not limited to, urea, polyethylene glycol, short chain fatty acid and their salts (sodium octanoate, sodium dodecyl sulfate), ethanol, Glyceryl monostreatrate, Isopropyl myristate, and Polysorbate surfactants.

In some embodiments, tight junction modifier/cell membrane permeability enhancers include, but are not limited to, anionic surfactants, non-anionic surfactants, charged polymers, dimethyl sulfoxide (DMSO), decylmethyl sulfoxide, tert-butyl cyclohexanol, fatty acids their esters and salts, ethanol, nicotinamide, urea, perfluoropolyether, monoterpene ketones, disodium citrate, succinic acid, alkyl saccharides, hyaluronidase and tris.

In another embodiment, the thermoreversible hydrogel comprises between 20% and 35% (w/w) EPO/PPO block copolymer and between 0.05% and 0.5% (w/w) hydroxypropylmethylcellulose (HPMC) or Polyvinylpyrrolidone (PVP).

In other embodiments the thermoreversible hydrogel comprises between 10% and 35% (w/w) EPO/PPO block copolymer and between 0.05% and 0.5% (w/w) hydroxypropylmethylcellulose (HPMC) or Polyvinylpyrrolidone (PVP) and between 0.01% and 2.5% (w/w) polyethylene glycol (PEG)-400; and the balance water.

In particular embodiments, the thermoreversible hydrogel composition of the first and second compositions is the same. In other embodiments, the thermoreversible hydrogel composition is different in the different compositions. For example, in some embodiments, the thermoreversible hydrogel composition of the first composition degrades more quickly than that of the second composition under physiological conditions. In other embodiments, the thermoreversible hydrogel composition of the second composition degrades more quickly than that of the first composition under physiological conditions.

The gelation properties of the thermoreversible hydrogel composition allow the first and second compositions to be administered in liquid form to the surface of an internal body cavity. Such administration can be by any method known to the art, using any device suitable to apply the subject compositions. For example, methods known to the art of intravesical instillation of an agent can be used to administer the compositions described herein to the surface of an internal body cavity.

In the methods described herein, a CCM is administered to an internal body cavity in a first composition. The results presented herein demonstrate that application of a CCM to urothelial cancer cells for a sustained period of time can synchronize a majority of the cells in a sample at a particular phase of the cell cycle, such as but not limited to the S phase.

In particular embodiments of the described methods, the CCM can be an agent that can synchronize contacted cells to S-phase or an S phase arresting agent, including, but not limited to, CDK4/6 inhibitors (such as, but not limited to, PD-0332991, LEE011, CINK4, Flavopiridol p276-00 and P1446A-05) and to small molecules such as hydroxyurea, alternol, resveratrol, fluorodeoxyuridine, thymidine dinucleotide pTpT and Zidovudine. Such molecules are known in the art to have a cytotoxic effect in addition to synchronizing cells in the S phase. For example, hydroxyurea is an antineoplastic agent commonly used to treat myeloproliferative disorders and other nonneoplastic conditions. Despite an intrinsic cytotoxic effect, it is shown herein that when administered sequentially with a second chemotherapeutic agent, not only are the cytotoxic effects significantly enhanced, but the dosage of the second agent needed for comparable effects when administered alone can be significantly reduced.

The second composition as described herein includes at least one anti-cancer agent such as a chemotherapeutic cytotoxic, anti-neoplastic, or anti-angiogenic agent. Examples of such agents for use in the described methods include, but are not limited to Mitomycin C, Apaziquone, BMS-181174, Gemcitabine, Cisplatin, 5-FU (5-fluorouracil) Doxorubicin, Valrubicin, Epirubicin, Pirarubicin, Methotrexate, and analogs thereof. It will be appreciated that the anti-cancer agent can be any known chemotherapeutic agent known in the art that is suitable for treatment of the cancer to be treated by the subject method. In particular examples, the agent is a small molecule agent. In other examples, the agent is a biological agent such as an antibody, protein, or nucleic acid based agent. Particular examples of nucleic acid-based agents used in anti-cancer therapies include nucleic acids for use in gene silencing (miRNAs, siRNAs, and the like), as DNA vectors expressing therapeutic RNAs and proteins.

As described herein, the described methods also allow for use of a lower concentration of chemotherapeutic agent than might otherwise be needed to produce a similar effect. As a result of the described methods 2, 3, 4, 5, 6, 7, 8, 9, 10 fold or less chemotherapeutic agent is needed in the second composition than might be needed to provide a similar cytotoxic therapeutic effect if the compound was not administered as described herein. It will be appreciated that different chemotherapeutic agents will have different dosing regimens depending on a particular subject, the cancer type, and their individual treatment needs. However, the surprising results provided herein allow for highly efficacious treatment simultaneous with decreased medication requirements.

The following examples are provided to illustrate certain particular features and/or embodiments. These examples should not be construed to limit the disclosure to the particular features or embodiments described.

EXAMPLES

Example 1: Methods

Cell Culture

The human bladder cancer cell lines, UM-UC-3 and RT-4, were obtained from the ATCC and grown in RPMI 1640 medium (Gibco) supplemented with 10% v/v fetal calf serum (Gibco), 100 U/ml penicillin and 100 g/ml streptomycin (Biological Industries). Cells were grown at 37° C., 5% $CO_2$ in a humidified atmosphere and harvested using 0.25% w/v trypsin, 0.02% w/v EDTA. Cells were washed in media to inactivate trypsin before reseeding or analysis.

Drug Treatment

Hydroxyurea concentrations were selected based upon concentration ranges known in the art. MMC concentrations were evaluated and an $EC_{50}$ value was calculated. Hydroxyurea was dosed at a range of 0.25-10 mM and MMC at a range of 0.625-160 μM. For some assays, MMC was assayed at the $1 \times EC_{50}$ value or at $0.5 \times EC_{50}$ value or at $2 \times EC_{50}$ value.

Flow Cytometery

A LSRII Flow cytometer or Cyan Flow Cytometer were used for determining DNA content and cell cycle distribution of UM-UC-3 and RT-4 cells. Cells were seeded in 6 well plates ($10^6$ cells/well) and incubated overnight. Cells were then treated with HU, MMC, and MMC or sequential administration of HU and MMC at the relevant concentrations for 2-48 hrs. When sequential treatment was done, the second drug was administered immediately or 2-48 hours following the wash of the $1^{st}$ treatment. The $2^{nd}$ treatment was then applied for additional 2-48 hrs before analysis. Cells were stained with propidium iodide (PI) following fixation before analysis using the argon ion laser set at 488 nm. PI staining was identified by using the red fluorescence (585+/−40 nm). In some experiments, cells harvested as for cell cycle determination were also stained with Annexin V or anti-activated Caspase-3 antibody for identifying apoptotic cells. Annexin V or activated Caspase-3 positive cells were identified using the green fluorescence (530+/−30 nm).

Cytotoxicity Assay:

UM-UC-3 and RT-4 cells were seeded into 96 well plates (10/well). Cells were incubated for 18-24 hours. Cells were treated with HU or vehicle control (DMSO) at the relevant concentrations for 18-24 hours. Cells were also treated with sequential administration of the MMC immediately after the wash of HU, or up to 48 hours followed the wash. Cells were exposed to MMC for up to 48 hours before addition of the XTT reagent (Biological industries). XTT assay for cytotoxicity was then performed and plates were analyzed in an ELISA reader at a wave length of 490 nm.

Example 2: Cell Cycle Regulation by HU

This example shows the synchronization of malignant cells at the S phase of the cell cycle by the addition and withdrawal of HU to cultured cells.

Unless otherwise indicated, methods were as described in Example 1. To monitor the effects of HU treatment on the cell cycle of bladder cancer cell lines, UM-UC-3 and RT4 cells were treated with 1 mM HU for 20 hours, an exposure time intended to replicate the sustained delivery of HU to a body cavity in the context of a hydrogel. HU treatment was followed by washing and further incubation of the cells, without drug, for 2-10 hours. Cell cycle was analyzed by flow cytometry as described.

Figure 1B:
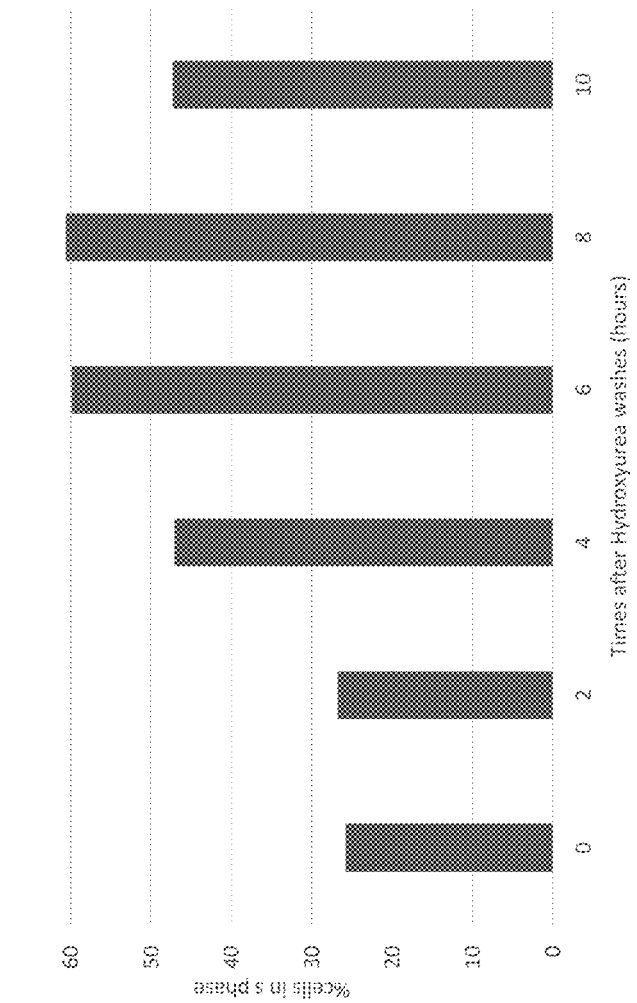

FIG. 1A shows the raw flow cytometry results for exposure of UM-UC-3 to HU, which are presented in a graphical format in FIG. 1B. Similarly, FIG. 2A shows the flow cytometry results for exposure of RT4 cells to HU, and which are represented graphically in FIG. 2B.

Figure 2A:
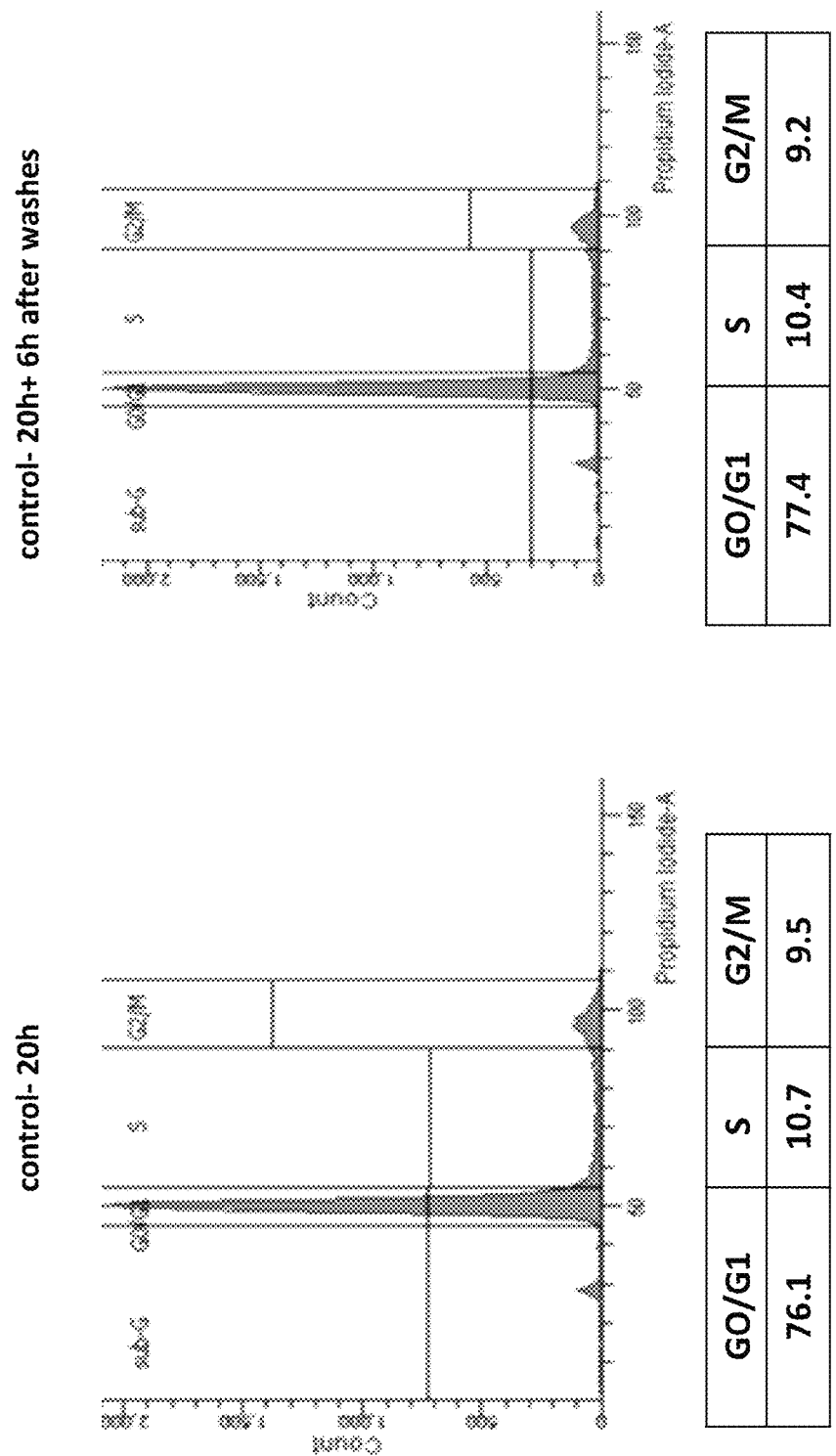
FIGS. 2A and 2B show cell cycle arrest in S phase following exposure of RT-4 cells to hydroxyurea.
Figure 2B:
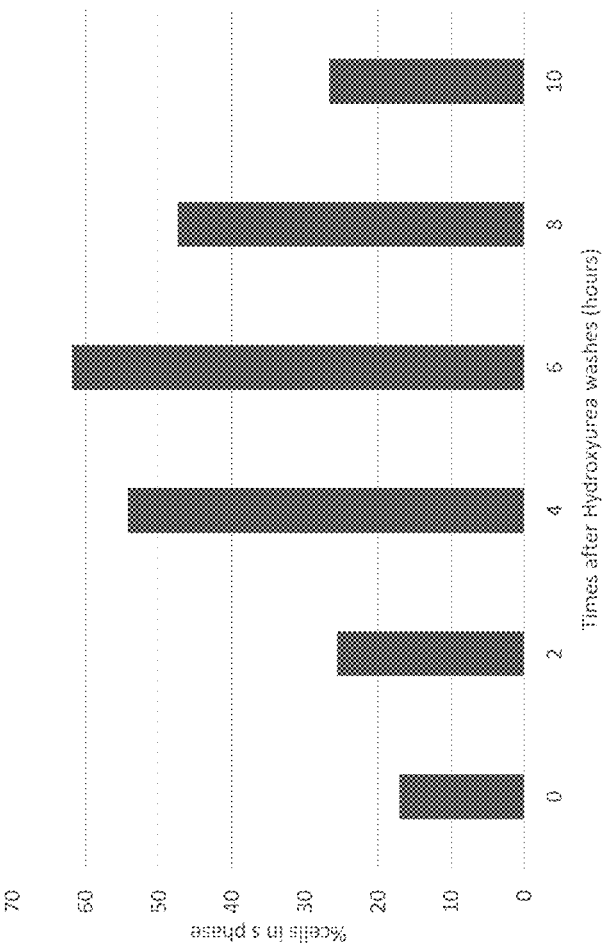

As shown in FIGS. 1A and 1B (UM-UC-3 cells) and FIGS. 2A and 2B (RT-4 cells), exposure to HU followed by drug withdrawal resulted in cell cycle synchronization at the S phase. Especially between 4 to 8 hours following the wash, the majority of cells in the sample are arrested at S phase.

These results demonstrate that sustained HU treatment followed by drug withdrawal, as can be produced by hydrogel delivery followed by its dissolution or wash, is effective at synchronizing and arresting bladder cancer cells at the S phase.

Example 3: Sequential Treatment with HU and MMC

This example shows that sequential, sustained treatment of bladder cancer cells with a cell cycle modulator (HU) and a chemotherapeutic agent (MMC) is significantly more effective at killing the cancer cells than treatment with either agent alone.

The effects of sequential sustained treatment by HU and MMC were tested in vitro on the UM-UC-3 bladder cancer cell line. Cells were pretreated with 1 mM HU (or DMSO-vehicle control) for 20 hours. Following a wash, cells were treated with 20 μM MMC (~$1 \times EC_{50}$ under these experimental conditions). Cell viability was analyzed 24 hours following MMC addition by XTT assay in an ELISA reader at a wave length of 490 nm. As indicated in Example 2, the extended exposure of the cultured cells to HU and MMC was designed to mimic the extended delivery of drug by the hydrogel vehicle. The percentage of viable cells presented was calculated from untreated cells with viability of 100%.

Figure 3:
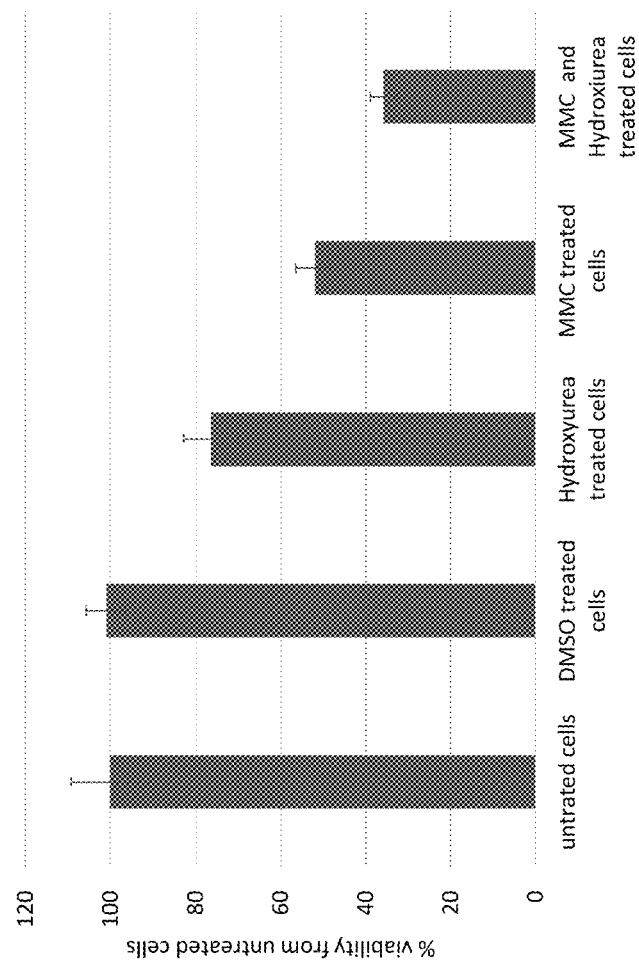
FIG. 3 is a histogram showing the viability of UM-UC-3 cells following treatment with Hydroxyurea alone, MMC alone and sequential addition of Hydroxyurea followed by MMC. UM-UC-3 cells were cultured in 96 well microculture plates. Cells were pretreated with 1 mM hydroxyurea (or DMSO-vehicle control) for 20 hours. Following wash, cells were treated with 20 µM MMC. Cell viability was analyzed 24 hours following MMC addition by XTT assay in an ELISA reader at a wavelength of 490 nm. The percentage of viable cells presented was calculated from untreated cells with viability of 100%.

As shown in FIG. 3, treatment with HU or MMC alone caused increased cell cytotoxicity (cell viability followed addition of HU or MMC was 76.5% and 51.9%, respectively). However, sequential sustained addition of the compounds increased cell death considerably (cell viability followed by sequential addition of HU and MMC was 35.9%). Results are presented in FIG. 3 and Table 1.

TABLE 1

Cytotoxicity of Sequential HU and MMC Exposure

| Drug treatment | Concentration of MMC | Concentration of HU | % Viability |
|---|---|---|---|
| MMC | 20 μM | NA | 51.9% |
| HU | NA | 1 mM | 76.5% |
| HU (20 hours) followed by MMC (24 hours) | 20 μM | 1 mM | 35.9% |

NA-not applicable

Figure 4:
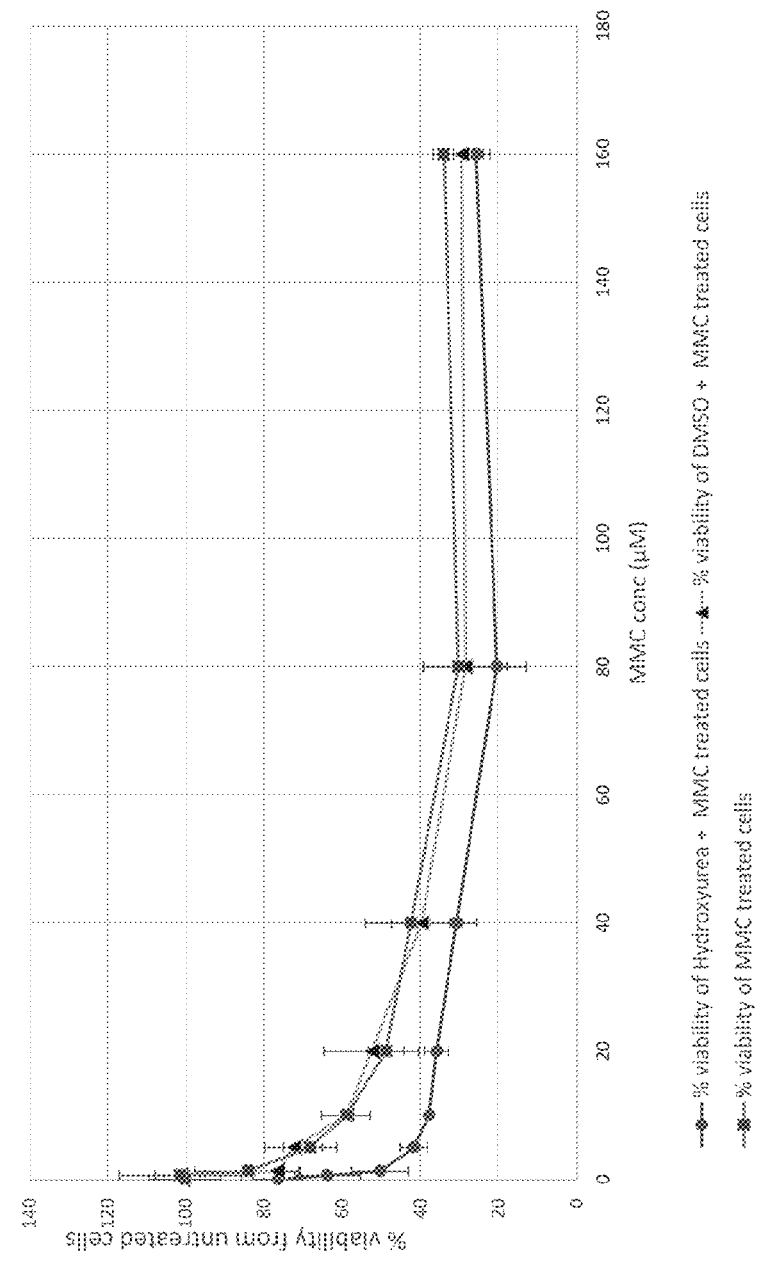
FIG. 4 is a graph showing UM-UC-3 cell viability of cells treated with increasing concentrations of MMC. Cells were either not pretreated, pretreated with DMSO (vehicle control), or pretreated with 1 mM hydroxyurea.

To determine the effect of MMC concentration in the sequential treatment method, the same experiment was performed in vitro on the UM-UC-3 cells as above, but with a range of MMC concentrations from 0-160 μM. The results are presented in FIG. 4. As shown in FIG. 4, sequential treatment with HU and MMC resulted in a greater cytotoxic effect than treatment of either HU or MMC alone. However, the benefit of the sequential treatment decreased, as expected, with increasing concentration of MMC. FIG. 4 also shows that at the lowest MMC concentrations, the greatest benefit of the sequential treatment is shown. These results strongly suggest that in addition to providing a greater cytotoxic effect, the sequential administration of HU and MMC would require significantly lower dosing of MMC to have a strikingly beneficial effect.

Example 4: Sequential Treatment with HU and MMC with a Washout Period

The previous example demonstrated that that sequential, sustained treatment of bladder cancer cells with a cell cycle modulator (HU) and a chemotherapeutic agent (MMC) is significantly more effective at killing the cancer cells than treatment with either agent alone. This example shows the beneficial effects of delaying treatment with MMC for several hours following removal of HU treatment.

As shown in FIGS. 1A and 1B, it was discovered that synchronization of bladder cancer cells by sustained HU treatment occurs over a period of several hours, following HU removal. To determine the influence of this phenomenon on the benefits of sequential treatment with MMC, the effect of applying MMC only after a delay following HU removal was tested.

UM-UC-3 cells were cultured in 96 well microculture plates. Cells were pretreated with 1 mM HU (or DMSO-vehicle control) for 20 hours. Cells were then washed. 2 hours following the wash, the cells were treated with 10 μM MMC 1×EC$_{50}$ under these experimental conditions) for 8 hours. MMC was then replaced by fresh medium. Cell viability was analyzed 48 hours following the addition of MMC by the XTT assay in an ELISA reader at a wave length of 490 nm. The percentage of viable cells presented was calculated from untreated cells with viability of 100%.

Figure 5:
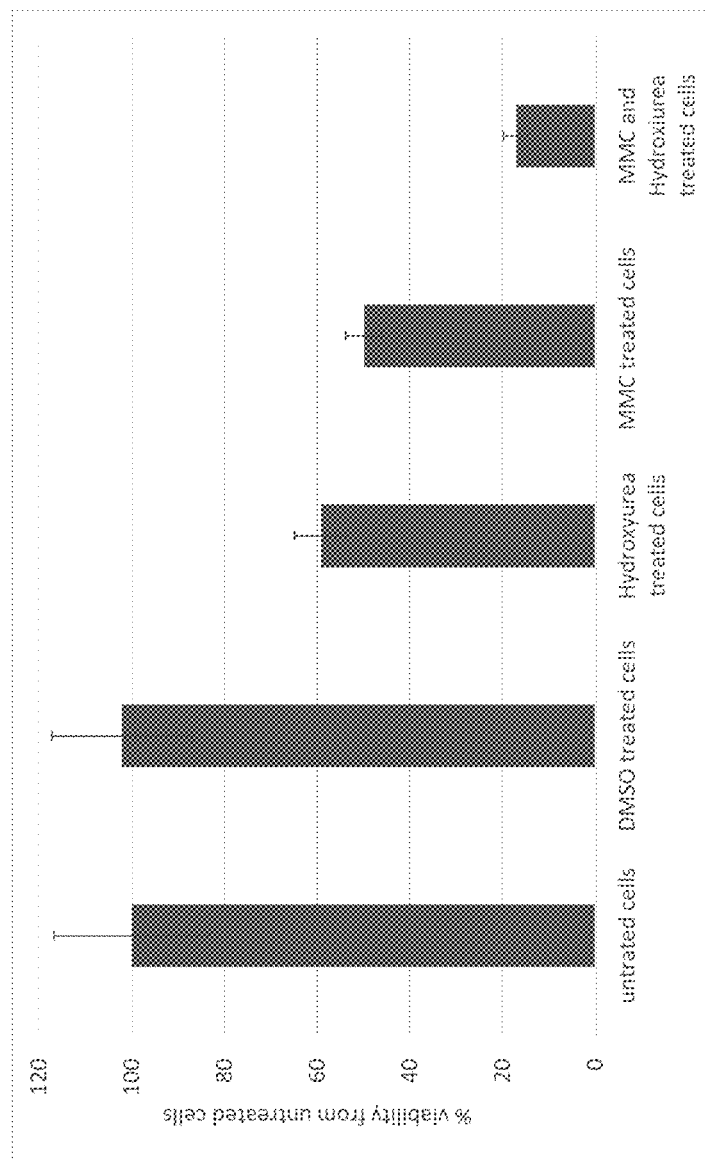
FIG. 5 is a chart showing the viability of UM-UC-3 cells following treatment with Hydroxyurea alone, MMC alone and sequential addition of Hydroxyurea followed by a period of wash and then incubation with MMC.

Similar to the results in the previous example, treatment with HU or MMC increased cell cytotoxicity (cell viability followed addition of HU or MMC was 59.6% and 49.9%, respectively). However, sequential addition of the compounds with an intervening wash and waiting period increased cell death considerably (cell viability followed sequential addition of HU and MMC was 17.1%). Results are presented in FIG. 5 and are also shown in Table 2.

TABLE 2

Cytotoxicity of Sequential HU and MMC Exposure with Intervening Delay

| Drug treatment | Concentration of MMC | Concentration of HU | % Viability |
|---|---|---|---|
| MMC | 10 μM | NA | 49.9% |
| HU | NA | 1 mM | 59.6% |
| HU (20 hours) followed by 2 hours wash and MMC (8hours) | 10 μM | 1 mM | 17.1% |

NA - not applicable

Figure 6:
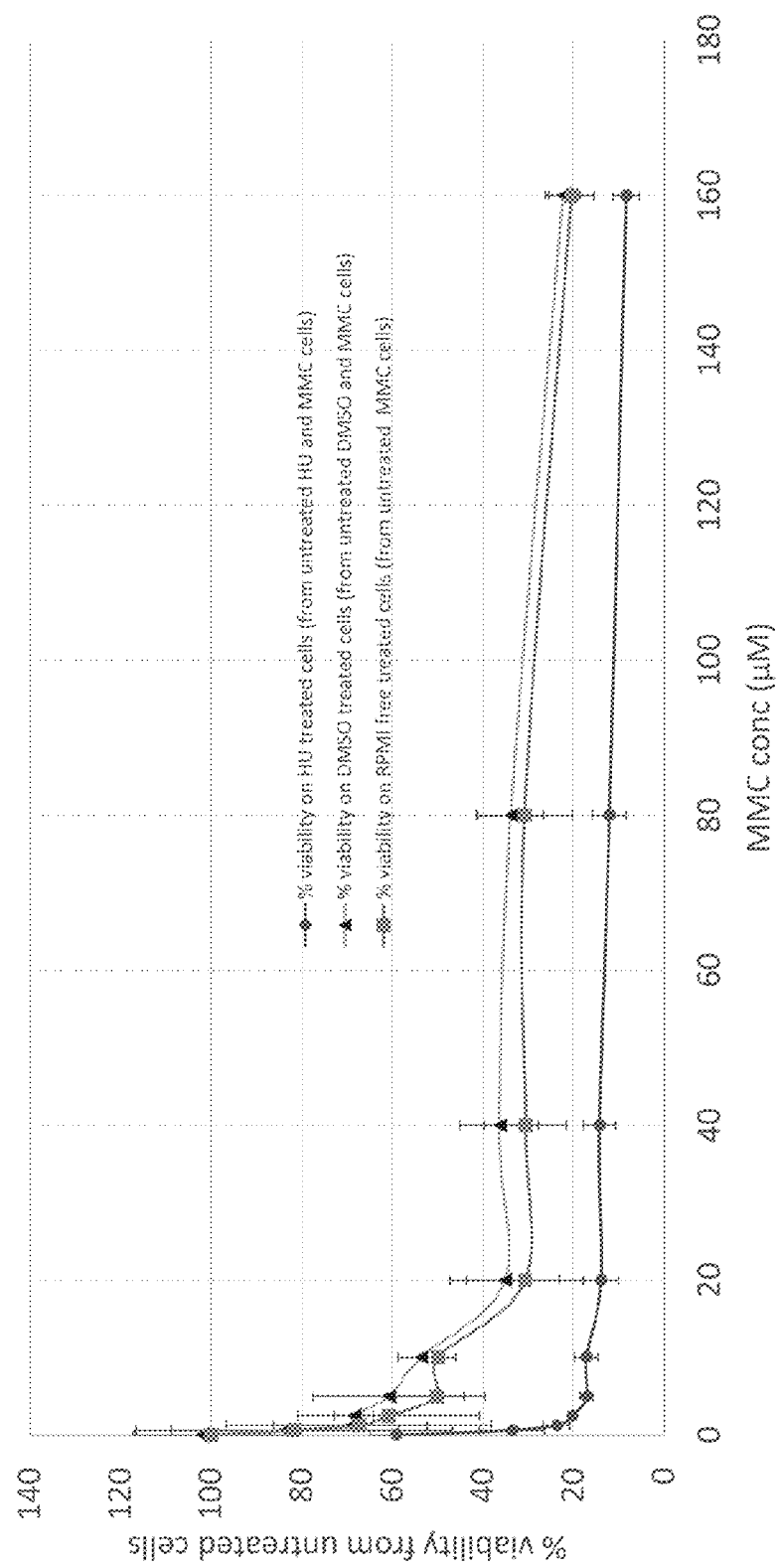
FIG. 6 is a graph showing UM-UC-3 cell viability of cells treated with increasing concentrations of MMC. Cells were either not pretreated, pretreated with DMSO (vehicle control), or pretreated with 1 mM hydroxyurea, following the same treatment method as used in FIG. 5 (HU treatment followed by wash period and then MMC treatment.

As in the previous example, the effect of MMC concentration was determined, and the same experiment was performed in vitro on the UM-UC-3 cells as above, but with a range of MMC concentrations from 0-160 μM. The results are presented in FIG. 6. As shown in FIG. 6, sequential treatment with HU and MMC resulted in a greater cytotoxic effect than treatment of either HU or MMC alone. However, the benefit of the sequential treatment decreased as expected, with increasing concentration of MMC. FIG. 6 also shows that at the lowest MMC concentrations, the greatest benefit of the sequential treatment is shown. It shows that introducing a period of waiting between HU and MMC treatments may allow for even smaller effective dosing of MMC.

Example 5: Shortened Sequential Treatment with HU and MMC with a Washout Period

In the previous examples, sustained exposure to HU and MMC was used to mimic the effects of administering the active agents to a subject with a hydrogel composition. This example presents the effects of a greatly shortened exposure to HU followed by MMC, as might be experienced by a patient provided with a non-hydrogel based treatment.

The methods used were as described in the other examples. Briefly, UM-UC-3 cells were cultured in 96 well microculture plates. Cells were pretreated with 1 mM HU (or DMSO-vehicle control) for 2 hours. Cells were then washed and 2 hours after the wash the cells were treated with 20 μM of MMC for 2 hours. MMC was then replaced by fresh medium. Cell viability was analyzed 48 hours following the addition of MMC by the XTT assay in an ELISA reader at wave length of 490 nm. The percentage of viable cells presented in the figures and table was calculated from untreated cells with viability of 100%.

Treatment with HU or MMC caused increased cell cytotoxicity (cell viability followed addition of HU or MMC was 86.1% and 47.1%, respectively). Sequential addition of the compounds increased cell death considerably (cell viability followed sequential addition of HU and MMC was 42.4%). Results are presented in FIGS. 7 and 8, and Table 3.

TABLE 3

Cytotoxicity of Short-Term, Sequential HU and MMC Exposure with Intervening Delay

| Drug treatment | Concentration of MMC | Concentration of HU | % Viability |
|---|---|---|---|
| MMC | 20 μM | NA | 47.1% |
| HU | NA | 1 mM | 86.1% |
| HU (2 hours) followed by 2 hours wash and MMC (2 hours) | 20 μM | 1 mM | 42.4% |

NA - not applicable

Figure 7:
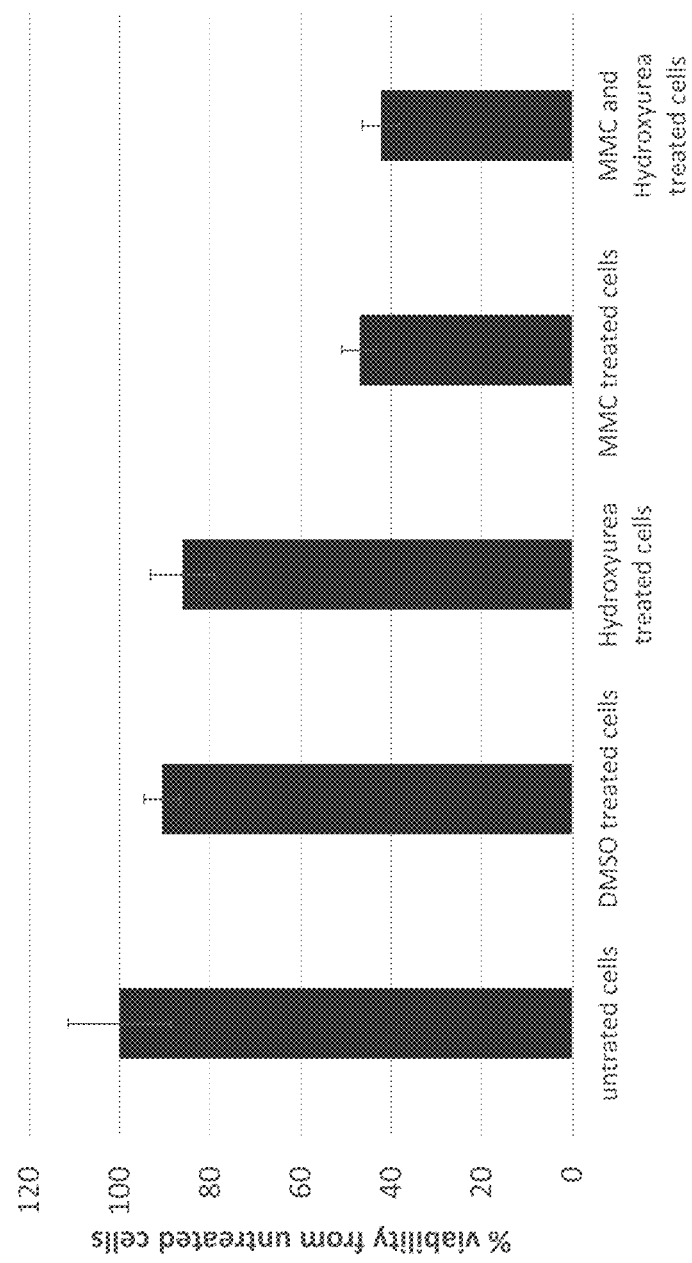
FIG. 7 is a chart showing the viability of UM-UC-3 cells following treatment with HU alone, MMC alone and sequential addition of HU for two hours, followed by a period of wash for two hours, and then incubation with MMC for two hours. The percentage of viable cells presented was calculated from untreated cells with viability of 100%.
Figure 8:
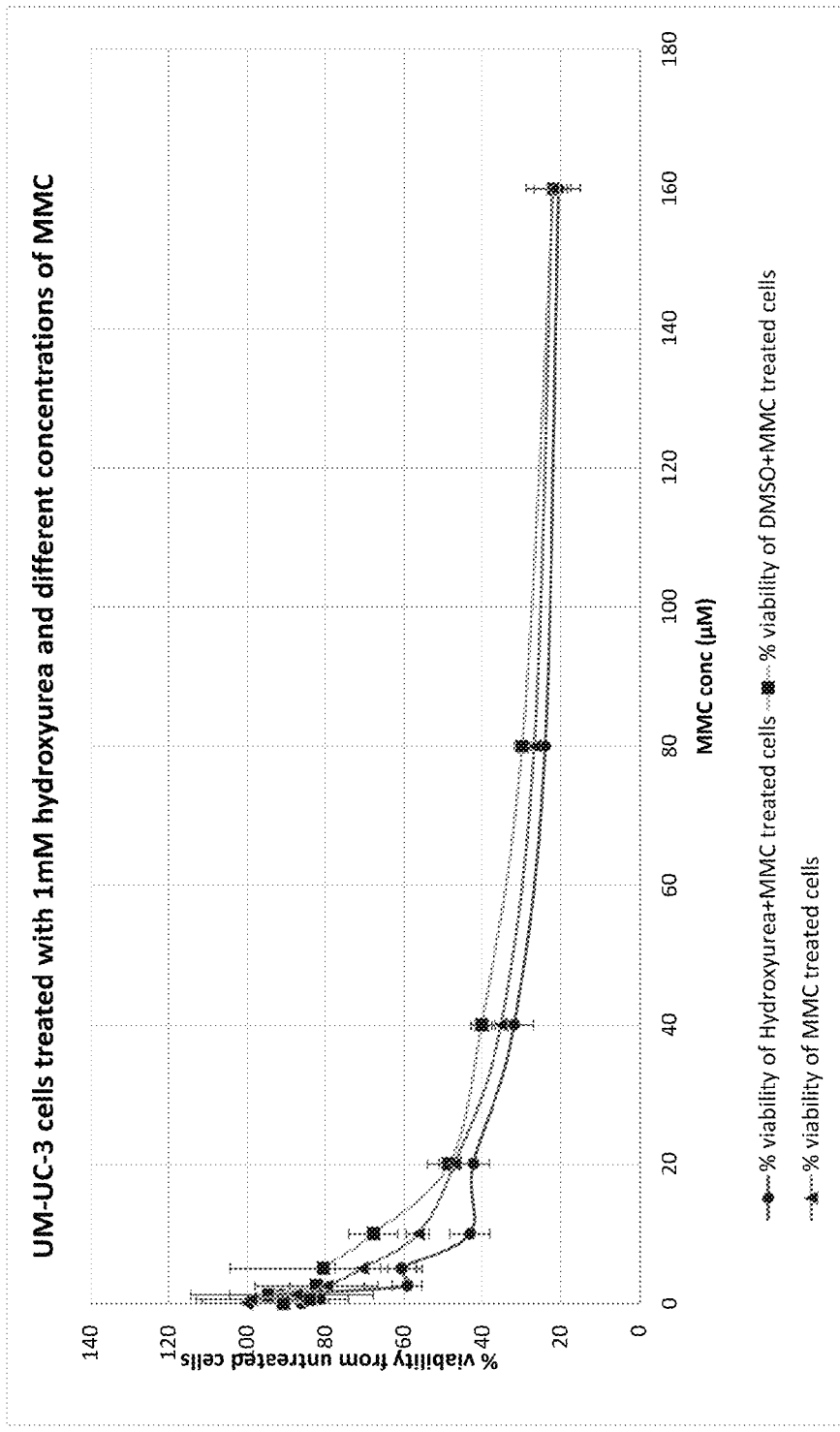
FIG. 8 is a graph showing UM-UC-3 cell viability of cells treated with increasing concentrations of MMC. Cells were either not pretreated, pretreated with DMSO (vehicle control), or pretreated with 1 mM hydroxyurea, following the same treatment method as used in FIG. 7 (two hour HU treatment followed by two hour wash period and then two hour MMC treatment.

As shown in FIGS. 7 and 8, and Table 3, treatment with MMC demonstrates a cytotoxic effect, however in the absence of a sustained administration, the effect is greatly diminished from that observed in Examples 3 and 4. Moreover, the concentration of MMC necessary to produce the effects observed in this Example was much greater than that needed in the previous examples. Taken together, these results support the understanding that a sustained treatment of HU followed by sustained treatment of MMC provides not only a superior effect, but also surprisingly provides the superior effect with a lower required concentrations of MMC.

Example 6: In Vivo Sequential Treatment of a Bladder Cancer

This example shows the treatment of bladder cancer in vivo with sequential administration of a thermoreversible hydrogel composition containing a cell cycle modulator, followed by administration of a thermoreversible hydrogel composition containing a cytotoxic chemotherapeutic agent.

For this experiment, the AY-27 invasive bladder cancer model will be used. Bladder tumors will be established in female F344 rats. Following anesthesia, rats' bladder will be pre-conditioned with instillation of 0.1 M hydrochloride (HCl). Immediately after bladder conditioning, AY-27 cells will be instilled into the bladder via a catheter and left indwelling for 60 minutes. Following catheter removal, the rats will be allowed to void spontaneously. On days 2 to 5 following the instillation of the cells, animals in the control group will not be treated, while animals that are treated with hydrogel containing HU will receive the first treatment session as follows: Instillation of 0.4-1 ml of hydrogel HU composition containing 0.01-10 mg/g B.W. In some groups, additional instillation(s) with HU will be done 2-24 hours following the first instillation. At the end of the treatment with the hydrogel-HU composition, animals that do not receive additional treatment with hydrogel containing MMC composition will only be exposed to additional sessions of treatment with the hydrogel HU composition, until necropsy at day 18 or earlier. Other animal groups will be either left untreated after treatment (for 2-48 hours) following the treatment with the hydrogel-HU composition before additional treatment with the hydrogel including MMC (0.4-1 ml), or treated immediately with the hydrogel containing the MMC. Other groups will only be treated with the hydrogel MMC composition without prior treatment with the hydrogel HU composition. MMC concentration in the hydrogel will be in the range of 0.05-8 mg/ml. In some groups, this instillation of the hydrogel containing the MMC will be repeated with one or more instillations of the same composition 2-24 hours following the first instillation. The whole sequence of instillations (only hydrogel containing HU, only hydrogel containing MMC and sequential administration of hydrogel containing HU and hydrogel containing MMC) may be repeated for additional 2-3 times in 2-4 days interval.

Rats will be sacrificed and subjected to necropsy. Bladders will be evaluated macroscopically, fixed and prepared for histopathological analysis at day 18 or earlier. The number of tumors, tumor stage (2002 TNM staging system) and tumor grade (2004 WHO/ISUP and WHO 1973 classification) will be evaluated.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for treating a urinary tract cancer, comprising:
   first administering to a subject in need thereof a first composition comprising a thermoreversible hydrogel composition and a therapeutically effective amount of at least one cell cycle modulator selected from the group consisting of hydroxyurea, alternol, resveratrol, fluorodeoxyuridine, thymidine dinucleotide pTpT and Zidovudine, PD-0332991, LEE011, CINK4, Flavopiridol p276-00 and P1446A-05; and
   secondly administering to the subject a second composition comprising a thermoreversible hydrogel composition and a therapeutically effective amount of at least one chemotherapeutic agent selected from the group consisting of Mitomycin C, Apaziquone, Gemcitabine, Cisplatin, 5-FU (5-fluorouracil) Doxorubicin, Valrubicin, Epirubicin, Pirarubicin, and Methotrexate,
   wherein the administration of the first and second compositions is by local administration to the urinary tract, thereby treating the urinary tract cancer.

2. The method of claim 1, wherein the urinary tract cancer is bladder cancer.

3. The method of claim 1, wherein the thermoreversible hydrogel composition of the first and second compositions is the same.

4. The method of claim 1, wherein the thermoreversible hydrogel compositions of the first and second compositions are different.

5. The method of claim 1, wherein the thermoreversible hydrogel composition of the first and/or second compositions comprises:
   20% to 40% (w/w) EPO/PPO block copolymer;
   0.05% to 0.5% (w/w) hydroxypropylmethylcellulose (HPMC) or Polyvinylpyrrolidone (PVP);
   0.1% to 2.5% (w/w) polyethylene glycol (PEG)-400;
   and the balance water.

6. The method of claim 1, wherein the cell cycle modulator is hydroxyurea.

7. The method of claim 1, wherein the chemotherapeutic agent is selected from the group consisting of: Mitomycin C, Gemcitabine, Cisplatin, and Doxorubicin.

8. The method of claim 1, wherein the local administration is by intravesical instillation.

9. The method of claim 1, wherein the second composition is administered to the subject 2-168 hours after administration of the first composition.

10. The method of claim 1, wherein the first composition is allowed to remain in the urinary tract for at least 2 hours, and further comprising washing the first composition from the urinary tract prior to administration of the second composition.

11. The method of claim 10, wherein the second composition is administered not more than 168 hours after the first composition is washed from the urinary tract.

12. The method claim 1, wherein the first and second compositions are provided to the urinary tract following surgery to remove the cancer.

13. A method for treating a urinary tract cancer, comprising:
   first administering to a subject in need thereof a first composition comprising a thermoreversible hydrogel composition and a therapeutically effective amount of hydroxyurea; and secondly administering to the subject a second composition comprising a therapeutically effective amount of at least one chemotherapeutic agent selected from the group consisting of Mitomycin C, Cisplatin, Gemcitabine and doxorubicin, wherein the administration of the first and second compositions is by local administration to the urinary tract, thereby treating the urinary tract cancer.

14. The method of claim 13, wherein the first composition is allowed to remain in the urinary tract for at least 2 hours, and further comprising washing the first composition from the urinary tract prior to administration of the second composition.

* * * * *